(12) United States Patent
Cropper et al.

(10) Patent No.: US 8,409,122 B2
(45) Date of Patent: Apr. 2, 2013

(54) BACK ORTHOSIS AND ORTHOTIC METHOD

(76) Inventors: Dean Cropper, Ashland, OR (US);
Tanner Cropper, Ashland, OR (US)

( * ) Notice: Subject to any disclaimer, the term of this patent is extended or adjusted under 35 U.S.C. 154(b) by 384 days.

(21) Appl. No.: 12/629,013

(22) Filed: Dec. 1, 2009

(65) Prior Publication Data
US 2010/0168630 A1   Jul. 1, 2010

Related U.S. Application Data

(60) Provisional application No. 61/119,022, filed on Dec. 1, 2008, provisional application No. 61/119,368, filed on Dec. 2, 2008.

(51) Int. Cl.
*A61F 5/00* (2006.01)
(52) U.S. Cl. ............................. 602/19; 128/96.1; 128/876
(58) Field of Classification Search .................. 602/5, 6, 602/12, 16, 19; 128/101.1, 100.1, 102.1, 128/96.1, 99.1, 876; 2/44, 309–311, 465, 2/467
See application file for complete search history.

(56) References Cited

U.S. PATENT DOCUMENTS

| | | |
|---|---|---|
| 61,487 A | 1/1867 | Volschwitz |
| 571,749 A | 11/1869 | Colton |
| 181,948 A | 9/1876 | Kleinschuster |
| 232,420 A | 9/1880 | Smith |
| 321,145 A | 6/1885 | Spencer |
| 321,146 A | 6/1885 | Spencer |
| 321,638 A | 10/1885 | Battershall |
| 386,642 A | 7/1888 | Mann |
| 601,446 A | 3/1898 | Mestler |
| 629,900 A | 8/1899 | Fosburgh |
| 746,563 A | 12/1903 | Mcmahon |
| 772,926 A | 10/1904 | Colton |
| 787,894 A | 4/1905 | Colton |
| 894,066 A | 7/1908 | Scarpa |
| 1,060,422 A | 4/1913 | Bowdish |
| 1,393,188 A | 10/1921 | Whiteman |
| 1,463,579 A | 7/1923 | Funck |
| 1,469,661 A | 10/1923 | Migita |
| 1,481,903 A | 1/1924 | Hart |
| 1,530,713 A | 3/1925 | Clark |
| 1,558,661 A | 10/1925 | Yeganian |
| 1,974,283 A | 9/1934 | Kendrick |
| 2,036,484 A | 4/1936 | May |
| 2,100,964 A | 11/1937 | Kendrick |
| 2,117,309 A | 5/1938 | Fritsch |
| 2,219,475 A | 10/1940 | Flaherty |
| 2,409,381 A | 10/1946 | Pease |
| 2,541,487 A | 2/1951 | Triplett |
| 2,554,337 A | 5/1951 | Lampert |
| 2,749,550 A | 6/1956 | Pease |
| 2,828,737 A | 4/1958 | Hale |
| 3,371,351 A | 3/1968 | Allain |
| 3,834,048 A | 9/1974 | Maurer |
| 3,927,665 A | 12/1975 | Wax |
| 3,945,376 A | 3/1976 | Kuehnegger |
| 4,099,524 A | 7/1978 | Cueman |
| 4,175,553 A | 11/1979 | Rosenberg |

(Continued)

*Primary Examiner* — Patricia Bianco
*Assistant Examiner* — Kari Petrik
(74) *Attorney, Agent, or Firm* — The Harris Firm

(57) ABSTRACT

A lumbar orthosis that includes first and second, separate, opposing and mating front attachment panels; and a separate, laterally adjustable, rigid lumbar compression piece configured for positioning only at the rear of a wearer, wherein pulling of a cord causes the brace both circumferentially to tighten and to concentrate compression and pressure of the separate, laterally adjustable, rigid lumbar compression piece directly and especially upon a spinal region of a wearer's back with the aid of a mechanical advantage dependant upon a number of apertures through which the cord or cords pass. An orthosis and method for correcting lumbar and thoracic back pain and disorders is also disclosed.

17 Claims, 9 Drawing Sheets

U.S. PATENT DOCUMENTS

| | | | |
|---|---|---|---|
| 4,470,417 A | 9/1984 | Gruber | |
| 4,475,543 A | 10/1984 | Brooks | |
| 4,508,110 A | 4/1985 | Modglin | |
| 4,541,419 A | 9/1985 | Osawa | |
| 4,574,789 A | 3/1986 | Forster | |
| 4,658,807 A | 4/1987 | Swain | |
| 4,696,291 A | 9/1987 | Tyo | |
| 4,862,878 A | 9/1989 | Davison | |
| 4,870,761 A | 10/1989 | Tracy | |
| 4,930,499 A | 6/1990 | Rowe | |
| 4,937,952 A | 7/1990 | Olivieri | |
| 4,964,401 A | 10/1990 | Taigen | |
| 5,012,798 A | 5/1991 | Graf | |
| 5,072,725 A | 12/1991 | Miller | |
| 5,074,288 A | 12/1991 | Miller | |
| 5,195,948 A | 3/1993 | Hill | |
| 5,226,874 A | 7/1993 | Heinz | |
| 5,258,017 A | 11/1993 | Myers | |
| 5,259,831 A | 11/1993 | LeBron | |
| 5,310,401 A | 5/1994 | Striano | |
| 5,328,447 A | 7/1994 | Kapounek | |
| 5,346,461 A | 9/1994 | Heinz | |
| 5,363,863 A | 11/1994 | Lelli | |
| 5,399,150 A | 3/1995 | Saunders | |
| 5,399,151 A | 3/1995 | Smith | |
| 5,433,697 A | 7/1995 | Cox | |
| 5,435,563 A | 7/1995 | Salvatore | |
| 5,437,617 A | 8/1995 | Heinz | |
| 5,466,214 A | 11/1995 | Calderon-Garciduenas | |
| 5,484,395 A | 1/1996 | Deroche | |
| 5,489,260 A | 2/1996 | Striano | |
| 5,499,965 A | 3/1996 | Sanchez | |
| 5,503,620 A | 4/1996 | Danzger | |
| 5,503,621 A | 4/1996 | Miller | |
| 5,591,122 A | 1/1997 | Yewer | |
| 5,599,286 A | 2/1997 | Labelle | |
| 5,599,287 A | 2/1997 | Beczak | |
| 5,620,412 A | 4/1997 | Modglin | |
| 5,634,891 A | 6/1997 | Beczak | |
| 5,690,609 A | 11/1997 | Heinze | |
| 5,693,006 A | 12/1997 | Slautterback | |
| 5,718,669 A * | 2/1998 | Marble | 602/5 |
| D394,707 S | 5/1998 | Tsubooka | |
| 5,782,782 A | 7/1998 | Miller | |
| 5,785,671 A | 7/1998 | Striano | |
| RE35,940 E | 10/1998 | Heinz | |
| 5,853,378 A | 12/1998 | Modglin | |
| 5,853,379 A | 12/1998 | Ostojic | |
| 5,857,988 A | 1/1999 | Shirley | |
| 5,967,998 A | 10/1999 | Modglin | |
| 5,984,885 A | 11/1999 | Gaylord | |
| 6,080,121 A | 6/2000 | Madow | |
| 6,099,490 A | 8/2000 | Turtzo | |
| 6,110,138 A | 8/2000 | Shirley | |
| 6,190,343 B1 | 2/2001 | Heinz | |
| 6,213,968 B1 | 4/2001 | Heinz | |
| 6,322,529 B1 | 11/2001 | Chung | |
| 6,336,908 B1 | 1/2002 | Slautterback | |
| 6,342,044 B1 | 1/2002 | Frangi | |
| 6,419,652 B1 | 7/2002 | Slautterback | |
| 6,425,913 B1 | 7/2002 | Chao | |
| 6,478,759 B1 * | 11/2002 | Modglin et al. | 602/19 |
| 6,517,502 B2 | 2/2003 | Heyman | |
| 6,554,785 B1 | 4/2003 | Sroufe | |
| 6,602,213 B1 | 8/2003 | Figley | |
| 6,602,214 B2 | 8/2003 | Heinz | |
| 6,676,617 B1 | 1/2004 | Miller | |
| 6,676,620 B2 | 1/2004 | Schwenn | |
| 6,749,579 B1 | 6/2004 | Schroder | |
| D492,787 S | 7/2004 | Weaver | |
| D496,108 S | 9/2004 | Machin | |
| 6,840,916 B2 | 1/2005 | Kozersky | |
| 6,886,553 B2 | 5/2005 | Yim | |
| 6,932,780 B2 | 8/2005 | Kozersky | |
| 6,951,547 B1 | 10/2005 | Park | |
| 6,964,644 B1 | 11/2005 | Garth | |
| 7,001,348 B2 | 2/2006 | Garth | |
| D518,895 S | 4/2006 | Weaver | |
| 7,025,737 B2 | 4/2006 | Modglin | |
| 7,037,284 B2 | 5/2006 | Lee | |
| 7,083,585 B2 | 8/2006 | Latham | |
| 7,118,543 B2 | 10/2006 | Telles | |
| 7,186,229 B2 | 3/2007 | Schwenn | |
| 7,201,727 B2 | 4/2007 | Schwenn | |
| 2001/0020144 A1 * | 9/2001 | Heinz et al. | 602/19 |
| 2001/0034498 A1 | 10/2001 | Heyman | |
| 2002/0068890 A1 | 6/2002 | Schwenn | |
| 2002/0148461 A1 | 10/2002 | Heinz | |
| 2004/0073150 A1 | 4/2004 | Roballey | |
| 2004/0077981 A1 | 4/2004 | Weaver | |
| 2004/0077983 A1 | 4/2004 | Reinecke | |
| 2005/0059917 A1 | 3/2005 | Garth | |
| 2005/0283102 A1 | 12/2005 | Schwenn | |
| 2006/0122547 A1 | 6/2006 | Stewart | |
| 2006/0161085 A1 | 7/2006 | Wikenheiser | |
| 2007/0049854 A1 | 3/2007 | Teimourian | |
| 2007/0073204 A1 | 3/2007 | Suarez | |

* cited by examiner

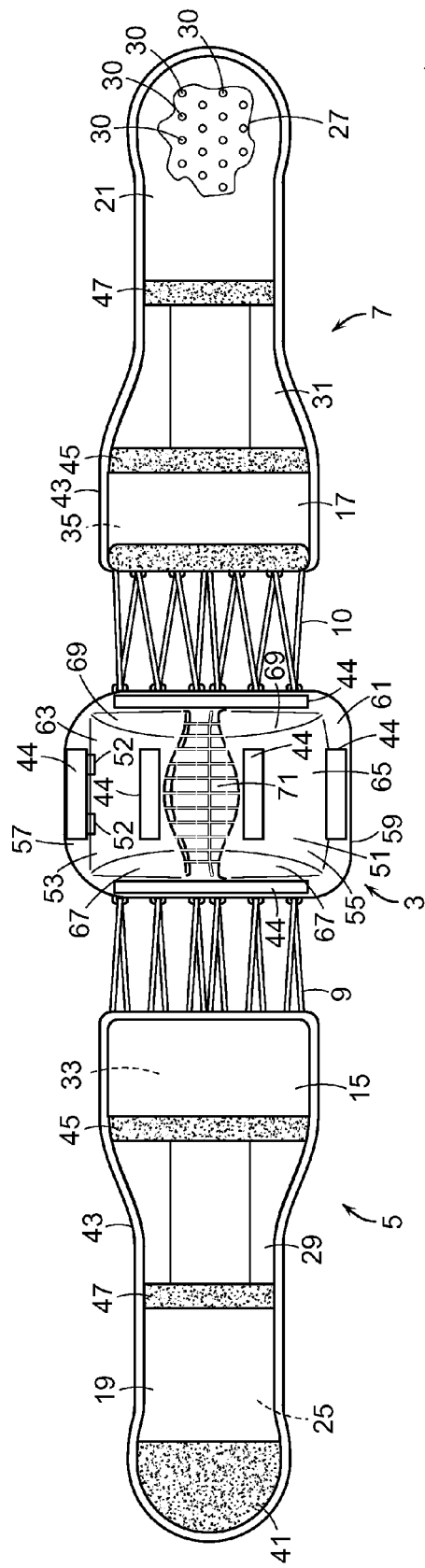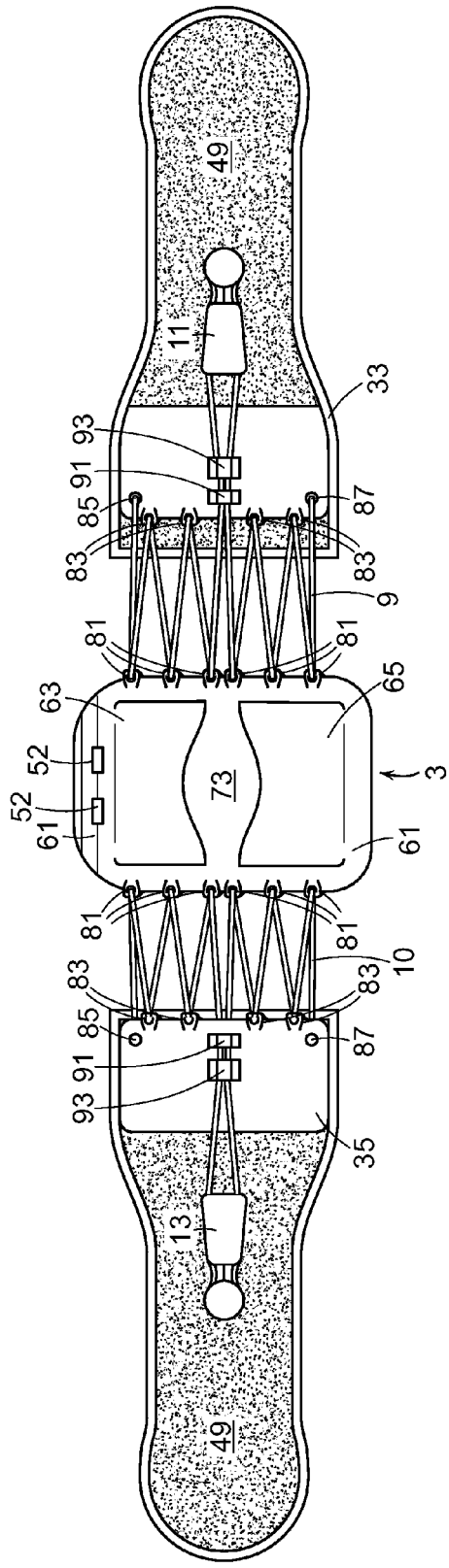
FIG. 1
FIG. 2

BACK ORTHOSIS AND ORTHOTIC METHOD

FIELD OF THE INVENTION

The present invention relates to a back brace and orthotic method. More particularly, the present invention relates to a spinal orthosis and orthotic method that provides an adjustable level of pressure to the lower back and high circumferential compression to the lower torso, particularly at the abdomen.

BACKGROUND OF THE INVENTION

Back braces are intended to alleviate or eliminate pain and suffering caused by various disorders along a person's spine. Some disorders more specifically relate to the lumbar region (vertebrae L1-L5), while others more specifically to the thoracic lumbar region (vertebrae T5 through S1). Others still stem at least in part from osteo-degenerative causes. The dynamic, integrated nature of various portions of the spine—as well as the many others variables that affect such disorders—make the occurrence of such disorders dependant on a large number of factors.

Several attempts to alleviate back pain include the application of a mechanical advantage to a circumferential torso brace. These systems have several advantages in respect to achieving at least some degree of temporary relief. Prior attempts to provide back support through a mechanical advantage fail to provide optimal pain relief or account for the shortcomings of providing only pure circumferential pressure as a factor in back pain stress, however. For example, U.S. Pat. Nos. 6,213,968 B1 and 6,676,620 B2, respectively entitled "Custom Fitted Orthotic Device" and "Modular Orthosis Closure System and Method" each disclose a single pulley system that draws the brace so as only to provide basic circumferential compression, without any integrated support in the lumbar area. They each have a piece that fits over the lumbar area, but none of these pieces has any connection to the workings of the brace as it is tightened other than simply being connected to the brace at the lumbar area.

U.S. Pat. No. 7,001,348 B1, entitled "Double Pulley Body Brace", discloses a single one-piece body panel and double pulley system, but likewise fails to provide integrated support or allow movement of its lumbar piece laterally in either direction.

Hence, the prior art fails to provide a back brace that provides a self-adjustable level of effective pressure directly to the spinal region of the lower back that is integrated with the tightening and loosening afforded by a mechanical advantage.

SUMMARY OF THE INVENTION

Thus, the present invention is directed to a spinal orthosis that provides an easy and effective means to reduce or eliminate back pain.

The present invention is alternately or additionally directed to a spinal orthosis—for chronic, acute, pre-operative, and/or post-operative persons—that can effectively be applied and adjusted by the wearer.

The present invention is alternately or additionally directed to a spinal orthosis with system components that broaden the brace's application such as allowing modification of a brace generally from a lumbo sacral orthosis ("LSO") to a thoracic lumbo sacral orthosis ("TLSO") or an osteoarthritic ("OA") brace, or both.

The present invention is also directed to an orthotic method that provides an easy and effective means to reduce or eliminate back pain.

The present invention is alternately or additionally directed to an orthotic method—for chronic, acute, pre-operative, and/or post-operative persons—that allows effective application and adjustment by the wearer.

The present invention is alternately or additionally directed to as orthotic method that implements system components that broaden a brace's application such as allowing modification of a brace generally from an lumbo sacral orthosis ("LSO") to a thoracic lumbo sacral orthosis ("TLSO") or an osteoarthritic ("OA") brace, or both.

One aspect of the present invention is directed to a back orthosis, comprising first and second, separate, opposing and mating front attachment panels, which are operatively attached to one another to form a circumferential enclosure about a wearer; and a separate, laterally adjustable, rigid lumbar compression piece configured for positioning only at the rear of a wearer and having: opposing first and second lateral sides, the first side connected along substantially its entire vertical length to the first, separate, opposing and mating front attachment panel by a first cord, and the second side connected along substantially its entire vertical length to the second, separate, opposing and mating front attachment panel by a second cord; a first set of apertures through which the first cord passes and is operatively pulled or allowed to loosen, respectively either: to draw the first side laterally closer to the first, separate, opposing and mating front attachment panel, and the first, separate, opposing, and the first separate, opposing and mating front attachment panel posteriorly closer to the first side, or to distance the first side laterally further from the first, separate, opposing and mating front attachment panel, and the first, separate, opposing and mating attachment panel further from the first side; and a second set of apertures through which the second cord passes and is operatively pulled or allowed to loosen, respectively either: to draw the second side laterally closer to the second, separate, opposing and mating front attachment panel, and the second, separate, opposing, and the second separate, opposing and mating front attachment panel posteriorly closer to the second side, or to distance the second side laterally further from the second, separate, opposing and mating front attachment panel, and the second, separate, opposing and mating attachment panel further from the second side; wherein pulling of the first cord and the second cord causes the brace both to circumferentially tighten and to concentrate inward compression of the separate, laterally adjustable, rigid lumbar compression piece directly and especially upon a spinal region of the wearer's back with the aid of a mechanical advantage dependant upon a number of apertures through which the first cord or the second cord passes.

In another aspect, pulling the first cord or the second cord causes relatively greater compression directly and especially upon a spinal region of a wearer's back than upon a region adjacent to the spinal region of a wearer's back.

In yet another aspect, the first set, the second set, or both first and second sets of apertures are formed by raised eyelets that are substantially parallel to the wearer's back surface when the separate, laterally adjustable, rigid lumbar compression piece is worn, and provide additional anchoring leverage actively to force the rigid lumbar compression piece specifically at the spinal region and so inwardly compress the spinal region of the wearer's back while keeping the first cord and/or the second cord spaced away from the wearer's back at a region adjacent to the spinal region of the wearer's back.

In still another aspect, the first and second, separate, opposing and mating front attachment panels have anterior portions that have greater rigidity than lateral sides of the orthosis, which provides an opposing vice-like frontal force diametrically opposed to the concentrated inward compression of the separate, laterally adjustable, rigid lumbar compression piece directly and especially upon a spinal region of a wearer's back.

In yet another aspect, the separate, laterally adjustable, rigid lumbar compression piece has a raised, beveled inner surface that operatively abuts against the wearer's spinal region.

In still another aspect, the rigid lumbar compression piece has a flat, curved, regular, irregular, or form-fitting inner compression surface and a generally flat, curved, regular, irregular, or form-fitting outer surface.

In yet another aspect, the rigid lumbar compression piece has at least four slots on each of the first and second lateral sides by which the respective first and second cords engage the lumbar piece so causing the lumbar piece to contour to a shape of the wearer's back.

In yet another aspect, the back orthosis further comprises at least one tensioning handle with respect to which the first cord passes and with respect to which a portion of the first cord changes its relative position in accordance with variations in upper and lower first cord material lengths, relative to one another, each of which running between the at least one tensioning handle and the first set of apertures.

In still another aspect, the first cord changes its position with respect to the tensioning handle at least in accordance with adjustable vertical and circumferential stationary tensioning handle attachment positions on the first or second, separate, opposing and mating front attachment panels, or first and second corresponding orthosis side portions.

In yet another aspect, the back orthosis further comprises a pad positioned between the wearer's back and the lumbar compression panel wherein foam within the pad flows.

In still another aspect, wherein the rigid compression panel comprises a horizontally and vertically centered reinforced center grid bordered by upper and lower hollowed out, beveled bowls, the bottoms of which push against the wearer's spinal region.

In yet another aspect, the first lateral side of the separate rigid lumber compression piece is immediately adjacent to at least one vertically centered aperture, through which the first cord passes through a final aperture on the separate rigid lumbar compression piece just before extending to a manually operated tensioning handle.

In still another aspect, the at least one vertically centered aperture is a pair of side-by-side apertures, through each of which one of two opposing lengths of the first cord passes.

In yet another aspect, the separate, laterally adjustable, rigid lumbar compression piece includes a central vertical axis about which independent horizontally disposed extensions project.

In still another aspect, the independent horizontally disposed extensions each correspond to at least one aperture of the first and second sets of apertures.

In yet another aspect, the independent horizontally disposed extensions operatively flex in accordance with varying contours of lumbar and thoracic spinal regions that vary from individual-to-individual, with a finger-like horizontal and transverse motion when engaged in tension by the first and second cords.

Another aspect of the present invention is directed to a back orthosis comprising a separate, laterally adjustable, rigid lumbar compression piece configured for self-adjustable positioning only at the rear of a wearer; twin opposing rigid panels for immobile placement upon opposing lateral sides of a spinal region of the wearer; a front abdominal piece, configured for immobile positioning upon an anterior side of the wearer; and at least two independent cinching systems, at least two of which are on opposing lateral sides of the separate, laterally adjustable, rigid lumbar compression piece configured for positioning only at the rear of the wearer, each providing a mechanical advantage for circumferentially tightening of the orthosis and applying a relatively greater force than a circumferential force specifically to four points of the wearer's torso; wherein the rigid lumbar compression piece and twin rear immobile rigid panels direct pressure radial to the wearer's spine; and wherein three of the four points are immobile while the forth point is laterally movable about a posterior lumbar side of the wearer, and the separate, laterally adjustable, rigid lumbar compression piece addresses the forth point of the wearer's torso.

Another aspect of the invention is directed to a back orthosis, comprising first and second, separate, opposing and mating front attachment panels; and a separate, laterally adjustable, rigid lumbar compression piece configured for positioning only at the rear of a wearer and having: opposing lateral sides, one such side connected along substantially its entire vertical length to the first, separate, opposing and mating front attachment panel by a cord, and the other such side connected along substantially its entire vertical length to the second, separate, opposing and mating front attachment panel by another cord or an elastic piece; a first set of apertures through which the cord passes and is operatively pulled or allowed to retract, respectively either to draw the one such side laterally closer to the first, separate, opposing and mating front attachment panel or to distance the one such side laterally further from the first, separate, opposing and mating front attachment panel; wherein pulling of the cord causes the brace both circumferentially to tighten and to concentrate compression of the separate, laterally adjustable, rigid lumbar compression piece directly and especially upon a spinal region of a wearer's back with the aid of a mechanical advantage dependant upon a number of apertures through which the cord or the another cord passes.

Another aspect of the invention is directed to an orthotic method comprising utilizing a back orthosis, comprising first and second, separate, opposing and mating front attachment panels, which are operatively attached to one another to form a circumferential enclosure about a wearer; and a separate, laterally adjustable, rigid lumbar compression piece configured for positioning only at the rear of a wearer and having: opposing first and second lateral sides, the first side connected along substantially its entire vertical length to the first, separate, opposing and mating front attachment panel by a first cord, and the second side connected along substantially its entire vertical length to the second, separate, opposing and mating front attachment panel by a second cord; a first set of apertures through which the first cord passes and is operatively pulled or allowed to loosen, respectively either: to draw the first side laterally closer to the first, separate, opposing and mating front attachment panel, and the first, separate, opposing, and the first separate, opposing and mating front attachment panel posteriorly closer to the first side, or to distance the first side laterally further from the first, separate, opposing and mating front attachment panel, and the first, separate, opposing and mating attachment panel further from the first side; and a second set of apertures through which the second cord passes and is operatively pulled or allowed to loosen, respectively either: to draw the second side laterally closer to the second, separate, opposing and mating front attachment panel, and the second, separate, opposing, and the second separate, opposing and mating front attachment panel posteriorly closer to the second side, or to distance the second side laterally further from the second, separate, opposing and mating front attachment panel, and the second, separate, opposing and mating attachment panel further from the second side; wherein pulling of the first cord and the second cord causes the brace both to circumferentially tighten and to concentrate inward compression of the separate, laterally adjustable, rigid lumbar compression piece directly and especially upon a spinal region of the wearer's back with the aid of a mechanical advantage dependant upon a number of apertures through which the first cord or the second cord passes.

BRIEF DESCRIPTION OF THE DRAWINGS

In the accompanying drawings, which form a part of the specification and are to be read in conjunction therewith, and in which like reference numerals are used to indicate like parts in the various views:

FIG. 2 is a plan view of an outer side of the back orthosis of FIG. 1;

FIG. 9a-1 is a cut away side view of clip tab 127 in FIG. 9a;

DETAILED DESCRIPTION OF THE INVENTION

Figure 3:
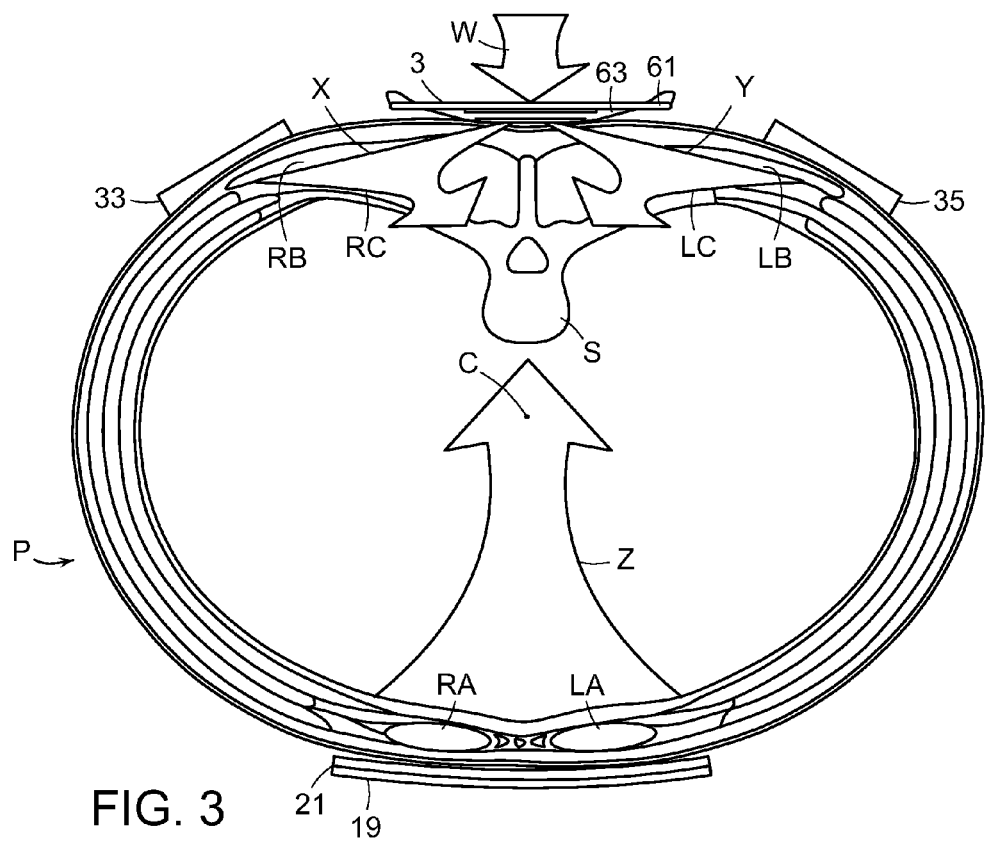
FIG. 3 is a top partial cross-sectional view of a person's torso, including several relevant anatomical features in a plane perpendicular to a vertical spinal axis, that are subjected to enhanced and uniquely applied posterior-to-anterior forces by the multi-positional lumber panel 3, rear panels 33 and 35, and attached rigid front panels 19 and 21 of the orthosis of FIG. 1.

As illustrated in the accompanying drawings and discussed in detail below, one aspect of the present invention is directed to a back orthosis that, when used, provides high circumferential compression to the lower torso with a high level of mechanical advantage. The back orthosis of this aspect nevertheless also applies a continued direct, adjustable amount of active support especially to the lower back, which can be finely tuned by lateral adjustment specifically to a particular area of pain.

In one embodiment, the back orthosis of the present invention provides a lumbo sacral orthosis ("LSO") 1. Referring to FIGS. 1 and 2, LSO 1 generally includes rigid separate rear lumbar panel 3, which is attached to each of right side attachment member 5 and left side attachment member 7 by respective separate right and left cords 9 and 10 to form a circumferentially attachable orthosis about a wearer's waist and torso. Right and left tensioning handles 11 and 13 can be used by any wearer to tighten and loosen cords 9 and 10, which run between rigid lumbar panel 3 and respective right 5 and left 7 side attachment members. After extensive research, it has been discovered moreover that LSO 1 thereby not only provides an overall system that increases compression about the torso, it provides a unique and surprisingly effective multiple-independent-point, symmetric anchoring system that specifically and inwardly compresses the wearer's spine and abdomen in a vice-like, diametrically-opposed, planar fashion, which unloads the spine to alleviate pain while allowing side-to-side movement of lumbar panel 3.

Rigid lumbar panel 3 fits directly over the lumbar spinal region of a wearer's back, including the spine and the soft tissue surrounding it. When applied as described below, it acts as a posterior wall to the lumbar spine in such a way that when the below-described cinching system is drawn, rigid lumbar panel 3 creates an inward force against the spine and soft tissue surrounding the spine. This helps to decompress the spine with the help of a continuous opposing force from at least one of rigid front segments 19 and 21, while lumbar panel 3 is free to laterally move side-to-side and about a wearer's spine in accordance with a particular spinal compression and pain relief for a given situation at a particular time.

Rigid lumbar panel 3 is specifically shaped and configured to maximize its effectiveness to accomplish these and other ends. Inner side 51 of panel 3 is generally shaped as an inverted rectangular dish comprising upper and lower symmetrically oriented bowls 53 and 55. Upper and lower side walls 63 and 65 run towards the panel's center approximately from perimeter (approximately 1-inch wide) lip 61 (which is at least approximately parallel to the wearer's back when worn and is rounded at its corners). Specifically from respective horizontal sides 57 and 59, walls 63 and 65 form relatively obtuse angles (with respect to immediately adjacent portions of lip 61) when compared to the angles formed between right and left lateral walls 67 and 69. Thus, compared with the relatively gently sloped walls 63 and 65, are beveled walls 67 and 69.

Dividing and reinforcing bowls 53 and 55 is a vertically and horizontally centered reinforcement section 71, specifically comprised of a hollow raised lattice work (defining approximately 48½ inch segments of a various assortment of full or truncated squares) that fills the space that occupies the dish volume otherwise defined by bowls 53 and 55. When compressed by application of LSO 1, panel 3 flexes along the vertical curvature of a wearer's spine, at which point this reinforcement section 71 provides added support and strength to lumbar panel 3. Section 71 also provides support and strength when panel 3 does not vertically flex. Posterior plate 73 adds further such support as well.

The resulting panel 3, which is generally vertically elongated, provides dual, centrally and inwardly thrust projections each having vertically and laterally beveled interior sides, both (1) generally to decompress a spine in a direction normal and perpendicular to the plane generally created by a wearer's back, but (2) also about the axis of the spine from between about 0 to about 45 degree (or from about 0 to about 5, 10, 15 or 20 degree) angles with respect to a position parallel to such plane.

Panel 3, especially when used with the cinching systems described below, projects inwardly and thereby applies particularly enhanced (as relative to the circumferential intra-cavity pressure otherwise exerted about a wearer) inwardly focused, concentrated force towards a wearer's spinal region. As described below, this relatively greater force against the spinal region is continually radial to the spinal region even as panel 3 is positioned at laterally varied locations from side-to-side across a wearer's back, because of the specially adapted beveled walls 67 and 69 of bowls 53 and 55, and the various possible, separately adjustable, angular positions of panel 3 with respect to the plane parallel to a wearer's back.

This configuration is especially and surprisingly effective when panel 3 is integrated into the workings of two or more laterally opposing independent and immobile cinching systems, as described below.

In one embodiment, two or more independent lateral, vertical, and/or diagonal cinching systems may be used with panel 3.

Panel 3 is also configured to accept intermediate self-attaching comfort pads, e.g., warm or cold gel pads, used for heat or cold therapy—as discussed further below. For example, hook or loop-friendly fabric strips 44 allow such removable attachment.

Panel 3 is optionally also configured with slots 52 that receive TLSO or OA orthosis attachments for secured removable attachment and therapy, also discussed below, though another embodiment has no such slots.

Right 5 and left 7 side attachment members each comprise a rigid back segment 15 (or 17), a rigid front segment 19 (or 21), and a flexible fabric lateral segment 29 (or 31). Rigid back segments 15 and 17 contain and confine rigid planar panel 33 (or 35), each of which is sewn into segment 15 (or 17) to keep the plastic planar panels 33 (or 35) from moving laterally, vertically, diagonally, or any combination thereof. Panels 33 and 35 are specifically bound by stitching in perimeter borders 43 and partitioning borders 45. This placement, which is immovable with respect to the rest of a respective attachment member 5 or 7, maintains proper anchor positioning of rigid back segments 15 and 17 with respect to a wearer's body. Rigid front segments 19 and 21, which have perforations 30 in panels 25 and 27, likewise contain and confine rigid front planar panels 25 and 27 for the same reasons at stitched perimeter borders 43 and partitioning border 47. As shown in FIG. 1, panel 27 has its outside nylon or polyester foam fabric 101 partially cut away. Exposed front rigid planar panels 25 (not shown) and 27 have regular ¼ inch circular perforations, which provide structural integrity.

Planer panels 33 and 35 each provide an independent rear anchoring point at a lateral side of a wearer's spinal region. They are not positioned directly adjacent to the wearer's spinal region. Rather, they are positioned directly over either right or left lateral muscle groups, i.e. over two muscle groups in the low back, the transversospinalis and intertranversarri portions of the wearer's back. This positioning provides additional inward pressure in parallel opposition to the force applied by rigid front segments 25 and 27. This positioning also prevents axial or rotational displacement of the LSO about the wearer's body when worn. Combined with rigid lumbar panel 3, they provide two symmetric points of a three point stabilizing system, as discussed further below. They further provide a guide and anchor position for the cord 9 and 10 cinching systems.

Flexible fabric lateral segments 29 and 31 circumferentially wrap around a wearer's torso, and so provide a flexible yet durable fabric connection between the rigid back segments 15 and 17, and the rigid front segments 19 and 21. Fabric segments 29 and 31, and the exterior of segments 15, 17, 19 and 21 are made from an external durable woven nylon formed as loop material laminated onto a polyester foam laminated onto a brushed nylon fabric. This protects the internal components, but any durable and strong relatively inelastic fabric may be used.

Monolithic, one-piece rigid lumbar panel 3 (including eyelets 81) is made entirely from injection molded nylon having a relatively firm hardness, but any rigid plastic material or similarly functioning material may be used, such as polyethylene, polyvinylchloride, or any other polymer or co-polymer resin. For example, treated natural wood, any foam injection resins (such as comprised of the polymers stated above), hard rubber, composites, metals, or many other materials may be used. In one embodiment panel 3 is made from Dupont® Zytel 66 nylon (as described in U.S. Pat. No. 6,756,429 herein incorporated by reference in its entirety) having a Shore D hardness of about 85, or from about 80 to about 90. Any material suitable for performing any or all of the functions stated herein may be used, however.

Rigid lumbar panel 3 is generally about ½ inch thick, but as described above, will vary in thickness in accordance with its unique shape and structural reinforcement. In its panel form, it may vary in general thickness from about ⅛ inch to about 2 or more inches, but of course carbon composite or high strength metal panels would allow for thinner or thicker panels to provide similar function.

Monolithic, one-piece rigid planar panels 33 and 35 (including eyelets 83) are made from injection molded nylon having a relatively firm hardness, but any rigid plastic material or similarly functioning material may be used, such as polyethylene, polyvinylchloride, or any other polymer or co-polymer resin. For example, treated natural wood, any foam injection resins (such as comprised of the polymers stated above), hard rubber, composites, metals, or many other materials may be used. In one embodiment panels 33 and 35 are made from Dupont® Zytel 66 nylon (as described in U.S. Pat. No. 6,756,429 herein incorporated by reference in its entirety) having a Shore D hardness of about 85, or from about 80 to about 90. Any material suitable for performing any or all of the functions stated herein may be used, however.

Panels 25 and 27 are made from ¼ inch injection molded polyethylene, but may be made from anywhere between about ⅛ and about ¾ inch at this hardness. As hardness varies, so may the relative thickness used, as long as it achieves some or all of the herein recited functions.

Nearly all of the components of LSO 1 are symmetrical about a plane running through the vertical central axis of rigid lumbar panel 3, except for an additional piece of hook-friendly fabric 41 used to attach right attachment member 5 over and onto left attachment member 7.

In an alternate embodiment, left attachment member 5 fits over right attachment member 7, however.

Outer sides 49 are covered in hook-friendly fabric, which mates with both loop-friendly fabric piece 41 on front segment 19 and loop-friendly material on the inner surfaces of right and left tensioning handles 11 and 13. Hook and loop fabric on any of the mating components may be reversed, or other suitable reversibly self-adjustable and attachable fabrics or fasteners may be used, however.

In another embodiment, attachment members 5 and 7 are identically equipped with various other types of attachment materials or devices suited for the adjustable attachment called for herein wherein members 5 and 7 provide a rotationally and vertically immobile fit.

In any case, the various components of attachment members 5 and 7—in particular rigid planar panels 33 and 35, and mating rigid front panels 19 and 21—when attached as part of LSO 1, are rotationally and vertically immobile with respect to the wearer's torso by virtue of the panel and fabric specifications noted above, and the relative placement and structural configuration described herein below.

LSO 1 provides at least three fixation points in a three-point stabilizing system. Referring to FIG. 3, rotationally and vertically immobilized rigid planar panels 33 and 35, and combined (when attached and partially cinched tight) rotationally and vertically immobilized rigid front panels 25 and 27, each provide one point of three immobile anchoring points in a four point anchoring system. These three points alone provide diametrically opposing vice-like parallel force particularly upon the abdomen and spine to decompress the spine. Movable lumbar panel 3 provides direct active force upon spine S, however. Right planar panel 33 provides direct force upon right transversospinalis, intertranversarri, interspinales, intertransversarii mediales, multifidi, and lumbar erector spinae areas RC, with relatively less pressure applied to an area just adjacent to the right side of the spine RB. Left planar panel 35 provides direct active force upon left transversospinalis, intertranversarri, Interspinales, intertransversarii mediales, multifidi, lumbar erector spinae areas LC, with relatively less pressure applied to area just adjacent to the left side of the spine LB.

Thus, lumbar panel 3 alone, or when coupled with right back panel 33 and left back panel 35, provides posterior force parallel to a wearer's back. While panel 3 may be adjusted from side-to-side, rotationally and vertically immobilized rigid front panels 25 and 27, and immobilized back panels 33 and 35 stay unmoved. This is illustrated by the unchanging inward but also directly opposing directional arrows W, X, Y, and Z, which are consistently, continually and continuously, approximately or precisely, radially directed or focused not strictly at intra-cavity center C of cavity P, but rather at spinal region S. This is achieved in part by applying force at specific points along the circumference of cavity P. Please note that such force is not primarily directed at muscles RB and RB, but rather bone structures RC, LC and S, and diametrically opposed abdominal muscles BA and LA. All four panels at all four anchoring points do this.

Figure 4:
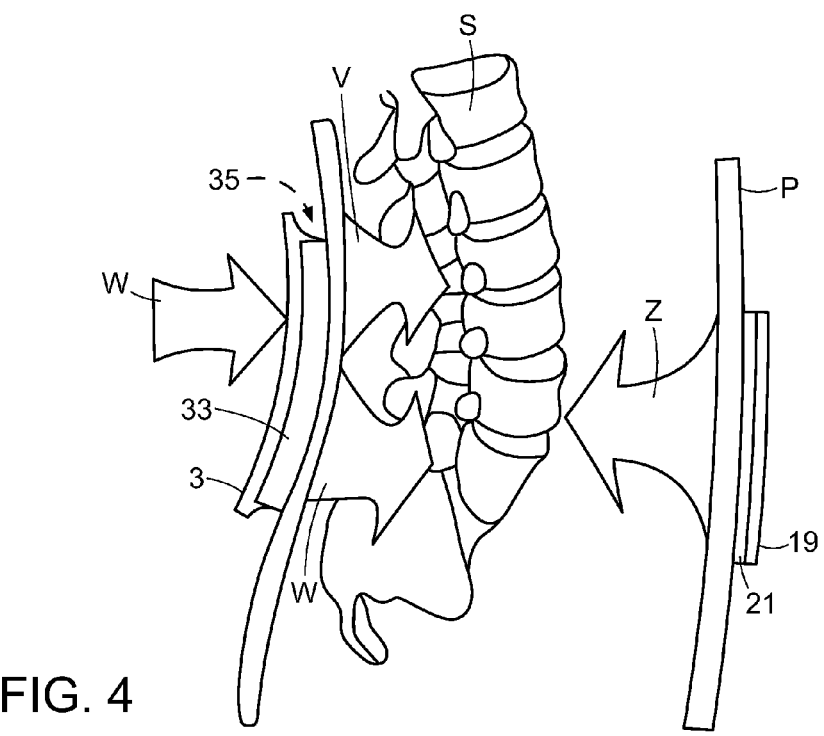
FIG. 4 is a side partial cross-sectional view of a person's torso including a whole spine in a plane sagittal to a vertical spinal axis, that is subjected to enhanced and opposing inward forces by the opposing lumbar panel 3, rear panels 33 and 35, and attached rigid front panels 19 and 21 of the orthosis of FIG. 1.

Referring to FIG. 4, the three immobile anchoring points upon which panels 25, 27, 33, and 35 address a wearer, and a movable anchoring point upon which (when attached) panel 3 addresses a wearer also provide various degrees of compression directed at spinal region S, that vary along the sagittal plane, e.g., a plane running vertical to divide right and left sides of cavity P. Cords 9 and 10 as shown below, may be cinched with varying degrees of tightness from the upper 53 to lower 51 sections of panel 3. As therapeutically needed, this variation of forces along the sagittal plane is illustrated by directional arrows V and W, which like arrows W, X, Y and Z, concentrate a greater amount of relative pressure directly upon and inwardly toward spine S, and not simply toward cavity center C. This is in addition to providing substantially greater diametrically opposed posterior and anterior, repeatedly and easily, self-adjustable parallel-vice-like force to specific portions of the wearer's torso.

Figure 5:
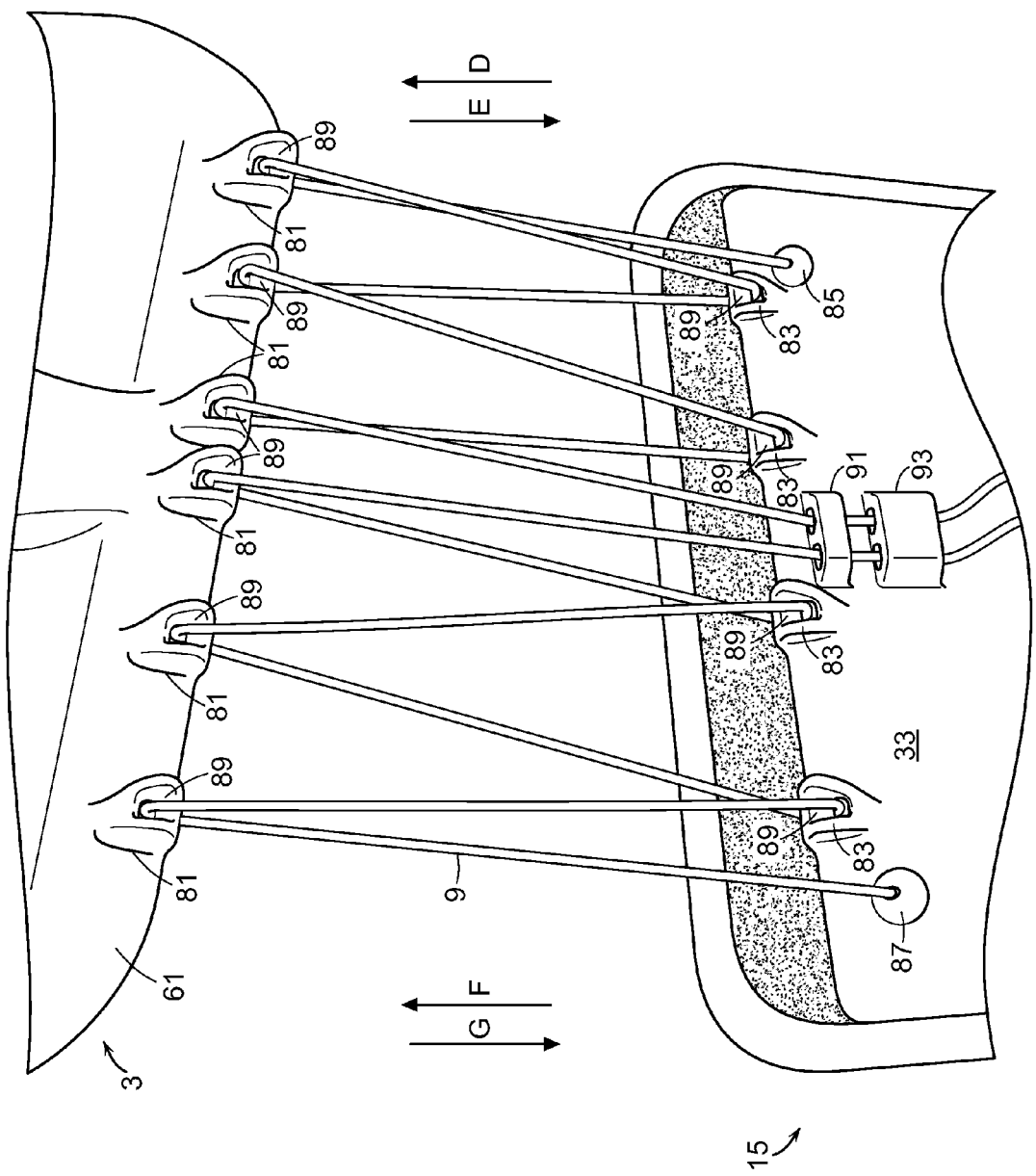
FIG. 5 is a partial lower perspective view of one of the cinching systems of the orthosis of FIG. 1.

Referring to FIG. 5, though three points of the four-point anchoring system are immobilized once LSO 1 is attached, lumbar panel 3 is employed as part of an self-adjustable, dual, independent cinching system that provides additional diametrically opposing parallel-vice-like force particularly upon the abdomen and spine to decompress the spine. Even after temporarily immobile attachment of LSO 1, nearly any conscious wearer—almost regardless of strength or condition—can adjust the side-to-side positioning and relative upper and lower force at which panel 3 is applied. Panel 3 is connected with two independent cord systems that can be move side-to-side because they are both independent and relatively raised from the back. This allows application of directed pressure on top of a particular acute or chronic pain location just lateral to the spine, for example in the case of a muscle spasm. At any lateral position, panel 3 consistently and continually applies force that is radial to the wearer's spine, and not simply the center of the torso cavity.

A set of six raised eyelets 81 on each side of panel 3 and four raised eyelets 83 on each of panels 33 and 35, further separate cords 9 (or 10) from LSO 1, and thus the wearer, thereby to provide added leverage to employ each of the dual independent, cinching systems. Each such system includes panel 3, cords 9 or 10, respective panels 33 or 35, and tensioning handles 11 or 13. One end of nylon or polyester cord 9 is knotted and fed through attachment hole 85 to secure it to panel 15. Cord 9 runs between the upper half of alternating eyelets 81 and 83, through cord guides 91 and 93 and through tensioning handle 11. Then cord 9 runs back through cord guides 93 and 91 and through the lower half of alternating eyelets 81 and 83—each time passing through acutely angled guide grooves 89.

Thus, raised eyelets 81 and the bowl portions of panel 3 provide several unique advantages. Lumbar panel 3 is compressed against a spinal region as cords 9 and 10 are being tensioned and the pressure is coming from side panels 33 and 35. At the same time, side panels 33 and 35 are being pulled up away from the back as cords 9 and 10 are being tensioned, due to the raised portions of lumbar panel 3. The two offset one another so the pressure under the side panels 33, 35 and lumbar panel 3 can be effectively the same. The effects on the underlying soft tissue can remain fairly constant under both areas.

In one embodiment eyelets 81 are replaced by simple holes having rounded and slick surfaces, or any other type of apertures through which cords 9 and 10 may pass to achieve a mechanical advantage.

In one embodiment, grooves 89 are angled from about 40 to 70 degrees, and in another embodiment from 45 to 65 degrees.

As such, panel 3 and panel 15 move and separate in accordance with the relative, and counteracting tightening and loosening of cords 9 and 10. This tightening, which may vary from the upper to the lower communicating portions of panel 3 and panel 15, will cause separately adjustable distancing along the entire vertical side of panel 3, as indicated by various directional movement arrows D, E, F, and G.

Figure 6A:
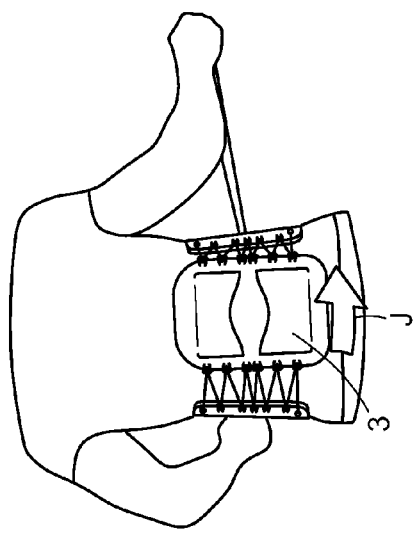
FIG. 6a is a rear view of a torso of a person wearing the orthosis of FIG. 1 wherein lumbar panel 3 is adjusted to apply force at the left side of the person's spinal region.
Figure 6B:
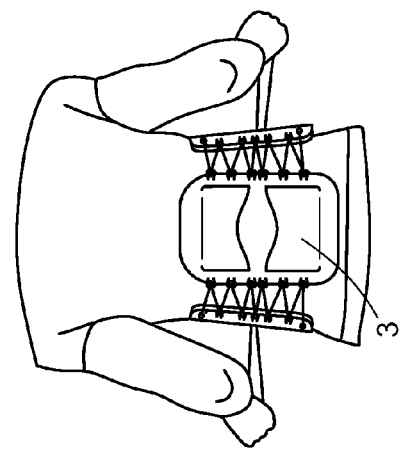
FIG. 6b is a rear view of a torso of a person wearing the orthosis of FIG. 1 wherein lumbar panel 3 is adjusted to apply force at the center of the person's spinal region.
Figure 6C:
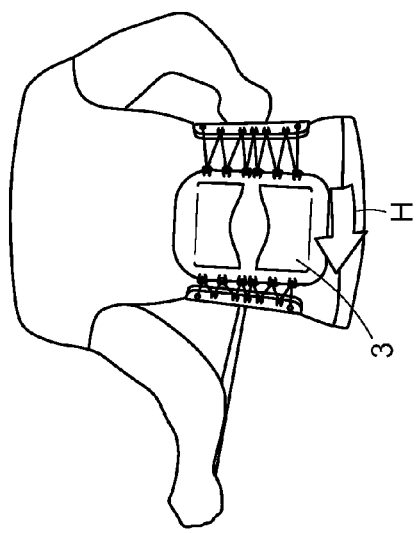
FIG. 6c is a rear view of a torso of a person wearing the orthosis of FIG. 1 wherein lumbar panel 3 is adjusted to apply force at the right side of the person's spinal region.

Referring to FIGS. 6a-c, configured as such each such cinching system allows side-to-side movement and adjustment of panel 3 about the wearer's spinal region while wearing LSO 1 and without having to remove LSO 1, as shown by directional arrows H and J. FIG. 6a, for instance shows a left-ward disposed position. FIG. 6b shows a centrally disposed position. FIG. 6c shows a right-ward disposed position. However, any intermediate position along this continuum is possible in accordance with a given condition at a particular moment in time. For example, in many cases acute back pain sufferers experience a list in the spine to compensate for pain from an injury. The ability laterally to re-position panel 3, even at a moment's notice, allows LSO 1 to provide support over the related para-spinal soft tissue that requires stabilization, thereby reducing the force and severity of such list.

Figure 7A:
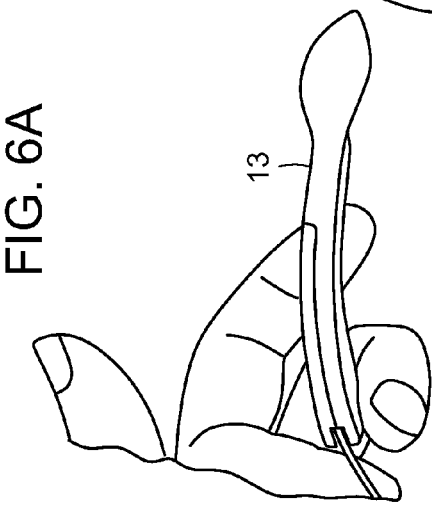
FIGS. 7a-c are respective side, top partial cut-away, and bottom views of a tensioning handle of the orthosis of FIG. 1.
Figure 7B:
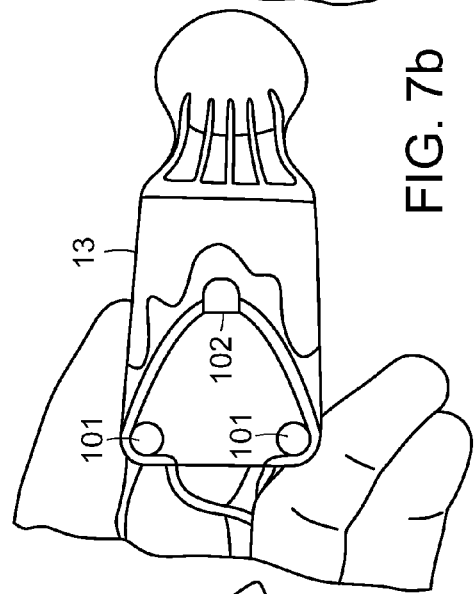
Figure 7C:
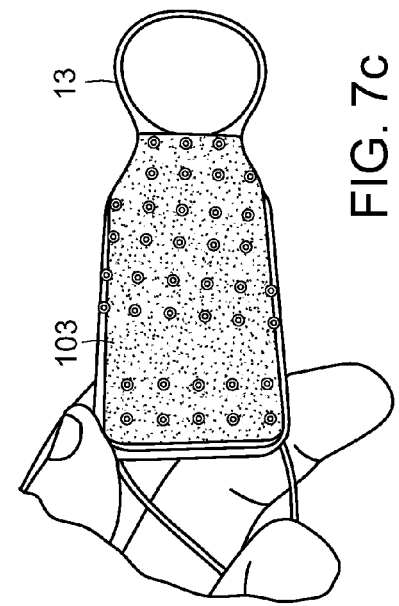

Referring to FIGS. 7a-c, curved symmetrically identical tension handles 13 (and 11 not shown) create an offsetting cord tension when drawn. In particular, cord 9 passes freely through tensioning handle 13 about internal connector 101. Each handle 13 has its own cord 10 used to cinch each side of LSO 1. Having cord 10 pass freely through tensioning handle 13 allows several advantages. First, it allows a wearer to self-adjust tension cord 10 between panels 3 and 35 (or 3 and 33 for handle 11) to adapt to different waist and hip ratios and sizes from wearer-to-wearer. It also allows self-adjustment of cord 10 to accommodate additional, or reduced, cord length (slack) when panel 3 is drawn to one lateral side versus the other so that the tensioning of handle 13 is always pulling on both sides of cord 10 with equal force.

Free passage of cord 10 also in turn provides meaningful and repeatable vertical and circumferential attachment positioning along the entire area of attachment members 5 and 7. Thus, equally distributed tension makes a lower vertical attachment position correspond to a longer upper length of cord, which tends to close the upper portion of the brace more, and vice versa.

Plus, this equally distributed, and greater more comfortable leverage, does not require handling the cords themselves. Limiting handling to tensioning handles 11 and 13 thus improves cinching ability by enhancing comfort and leverage—for all users. Curved handles also contour about a torso so as to lay flat when attached to attachment members 5 or 7 by hook fabric 103.

In one embodiment, both ends of cord 10 retract within tensioning handle 13 by the installation of suitable twin spring-loaded cord retraction devices. Such an installation, though independently taking-in cord slack on both sides of a handle, will not necessarily offer all of the advantages of the above-mentioned device, however.

Figure 8B:
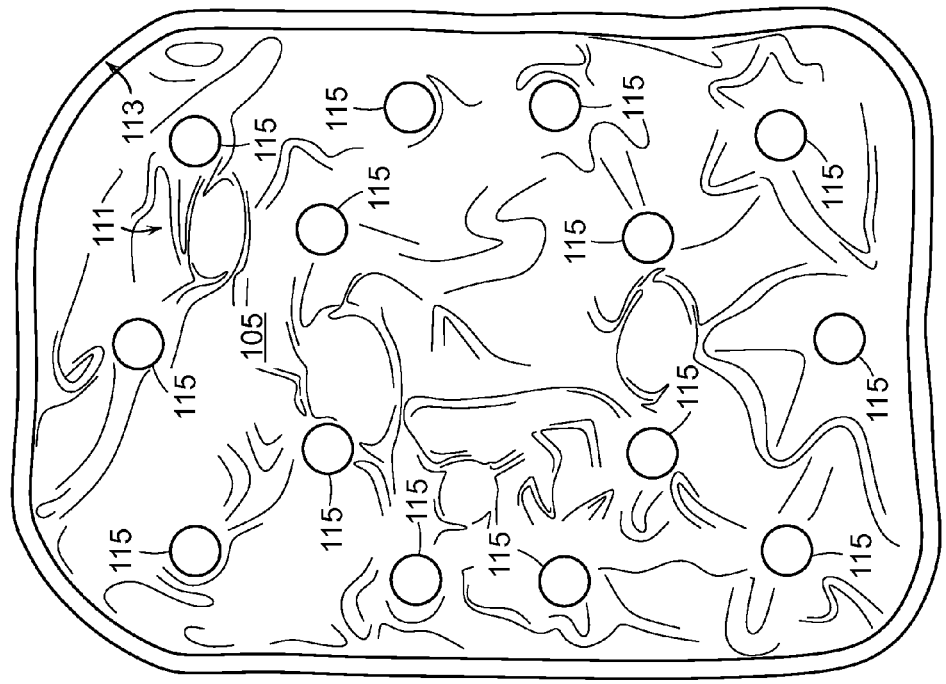
FIGS. 8a and b are respective attachment and application sides of a foam lumbar pad, according to the present invention.
Figure 8A:
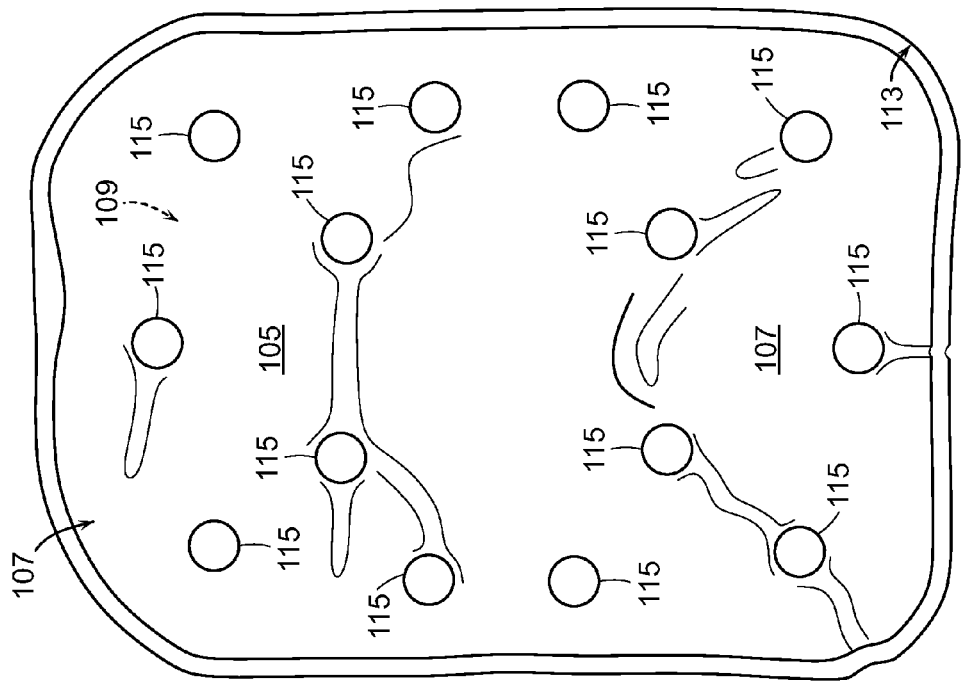

Referring to FIGS. 8a and b, hot or cold gel pads (not shown), or foam pad 105 containing flowing foam, may be attached to the inner side of panel 3 for example by hook-friendly fabric 107, which covers most of one side of pad 105. Side panels 109 and 111, which are made from a polyurethane film laminated to a brushed nylon fabric, are thermally bonded along edge 113 and circular press-points 115. As seen in FIG. 8b, pad 105 contains a paste-like foam, made by Tekpad™ (as described, e.g., in U.S. Pat. No. 6,583,199 herein incorporated by reference in its entirety), that fills in the lower profile areas of a wearer's lumbar spine when worn in conjunction with LSO 1. However, any material suitable for filling a void into which it flows may be used, including other fluids and gases of various densities.

Figure 9:
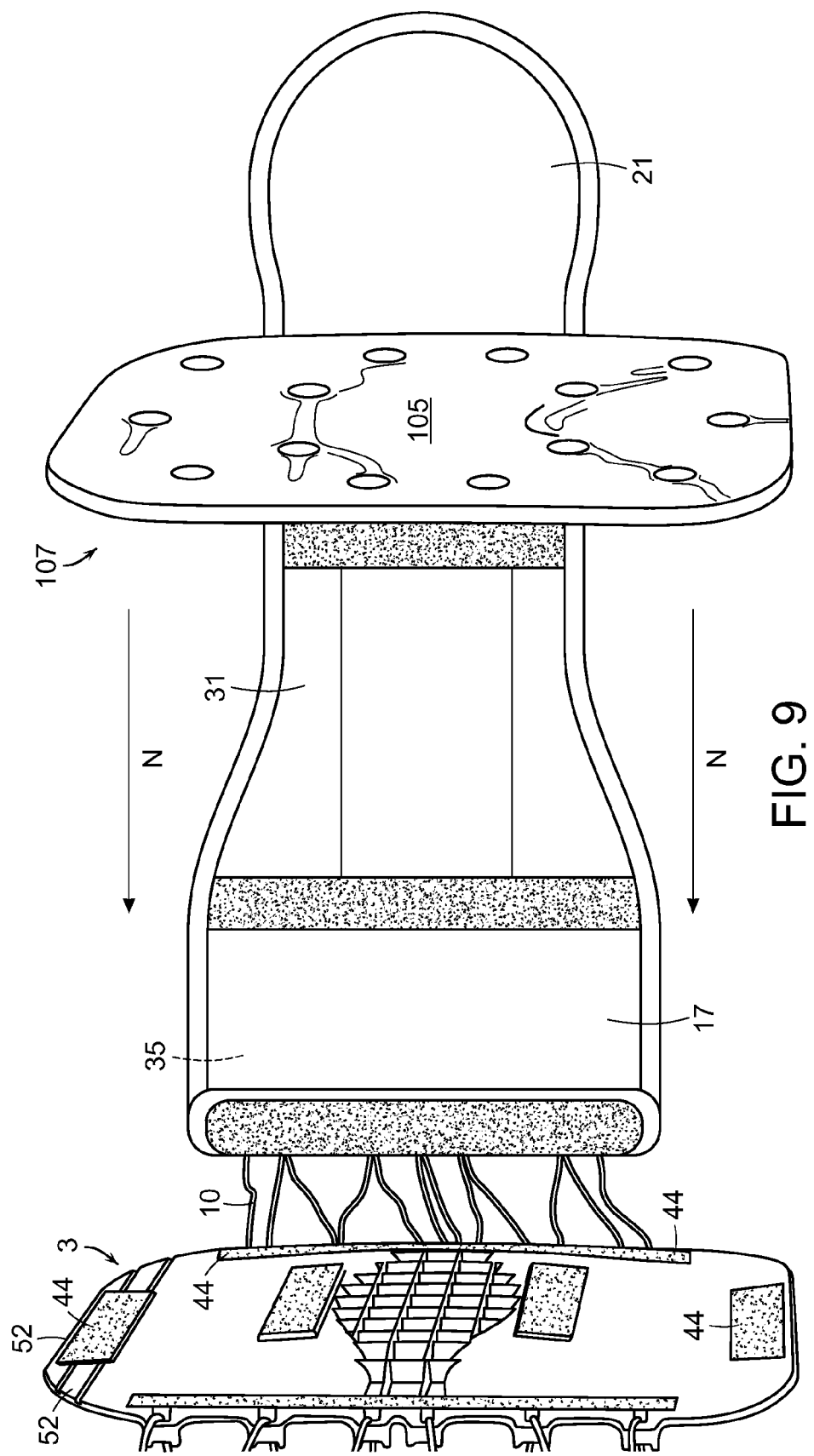
FIG. 9 is a partial side assembly view of the orthosis of FIG. 1 and the foam lumbar pad of FIGS. 8a and 8b.

Referring to FIG. 9, pad 105 attaches to panel 3 as shown in accordance with direction arrows N.

Referring to FIG. 9a, thoracic lumbo sacral orthosis ("TLSO") attachment plate 121 having apertures 125, and made from injection molded nylon, fits on the same inner side of panel 3 to form a thoracic lumbo sacral orthosis. Attachment plate 121 is a prefabricated piece that accepts panel 3 by a snap fit. Plastic clip tabs 127 reversibly snap into slots 52 (see FIGS. 1 and 2) on panel 3.

Figure 9B:
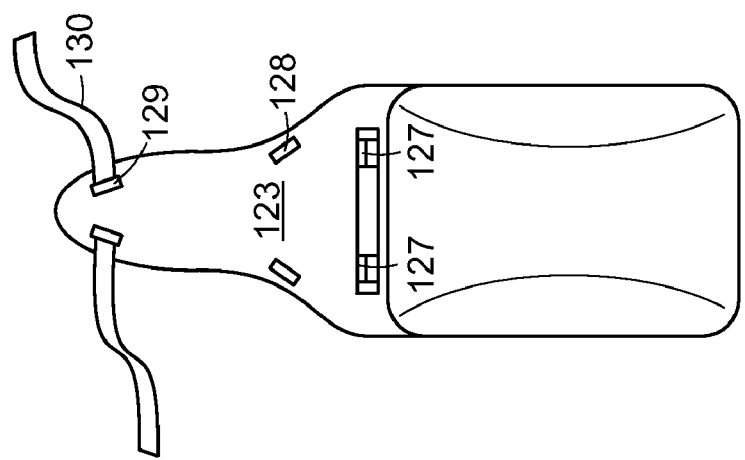
FIG. 9b is a plan view of an attachment side of another embodiment of a thoracic lumbo sacral attachment panel, according to the present invention.
Figures 1, 9A:
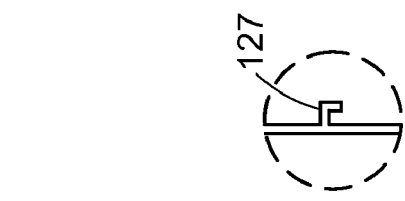
FIG. 1 is a plan view of an inner side of a back orthosis with a partial cut-away view of a perforated rigid front panel, according to one embodiment of the present invention.
FIG. 9a is plan view of an attachment side of a thoracic lumbo sacral attachment panel, according to the present invention.
Figure 9A:
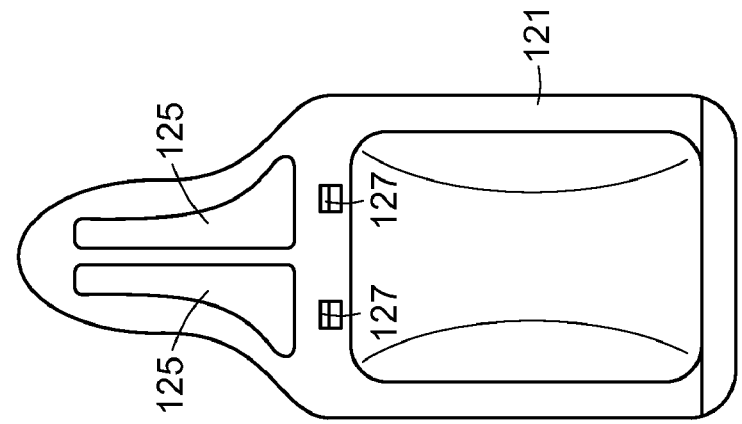

Referring to FIG. 9b, in an alternate embodiment, TLSO attachment plate 123 comprises a solid upper plate without apertures. Buckle or other attachment point 128 accepts strap 130 after strap 130 is attached from slots 129 and wrapped around a wearer's, e.g., shoulders and armpits.

Figure 10:
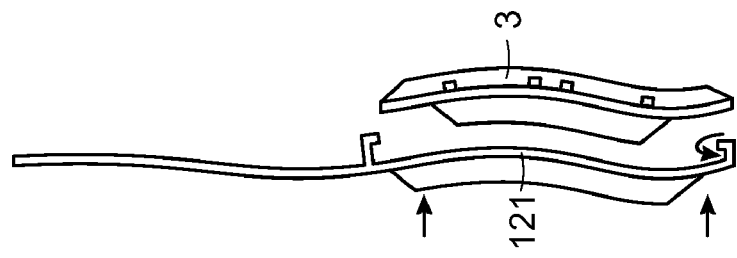
FIG. 10 is a side view of the lumbar panel 3 of FIG. 1 and the thoracic lumbo sacral attachment panel of FIG. 9a, as curved along their lengths when in use.

Referring to FIG. 10, in either embodiment lip 131 fits over the bottom edge of panel 3 so that clip tabs 127 may snap into slots 52. Panel 3 and attachment plate 123 fit together so that they both contour to the curvature of a spine during their application. This drawing, for example, shows a curve when the wearer's lumbar region is convex, such as when bending over.

In one embodiment, an orthoarthritic, thoracic fractures and thoracic surgeries attachment panel is similarly attached, in particular to afford posterior application of proximal ends of straps that run over a wearer's shoulders and/or around the armpit area for attachment at their distal ends upon the orthoarthritic, thoracic fractures and thoracic surgeries panel.

Figure 11A:
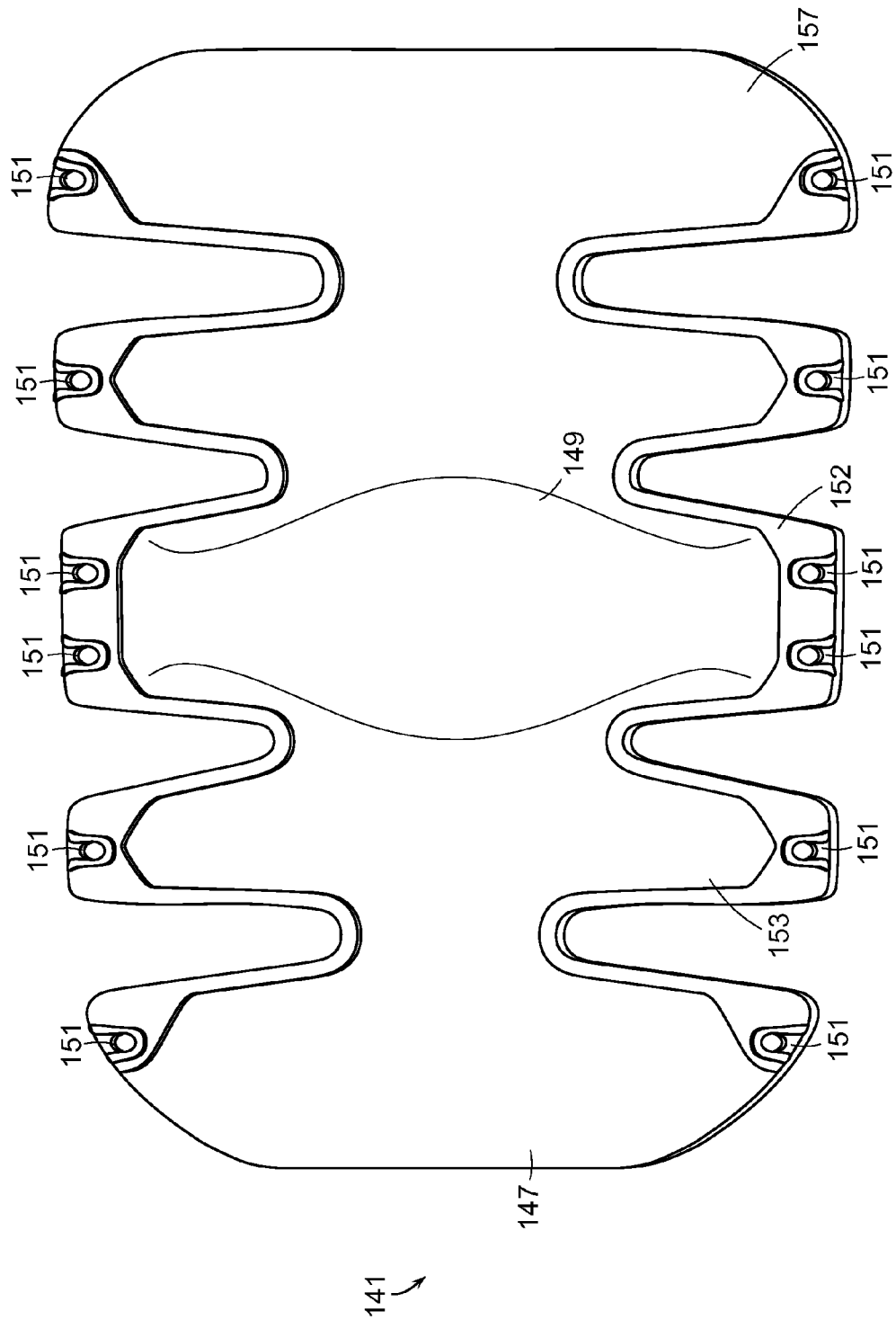
FIG. 11a is a plan view of the posterior side of one embodiment of a flexible multi-positional lumber panel, according to the present invention.
Figure 11B:
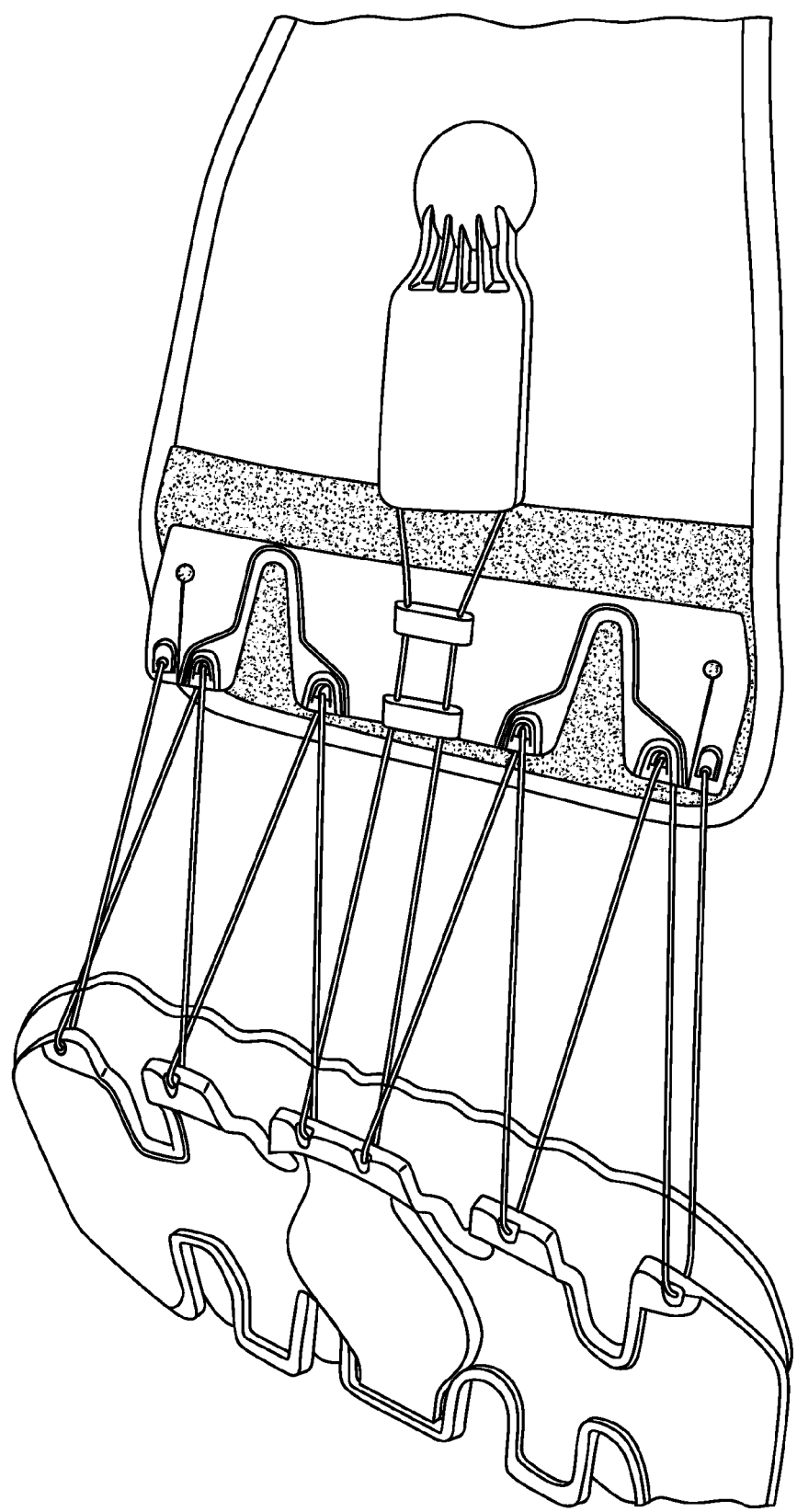
FIG. 11b is a perspective view of the lumbar panel of FIG. 11a and a foam pad, as incorporated into an alternate embodiment of the back orthosis of FIG. 1.

Referring to FIGS. 11a and 11b, in one embodiment panel 141 is used in place of panel 3. Panel 141 generally has the same outside perimeter shape and size, and material composition, hardness and thickness, as panel 3, but instead of two bowls its inner side is generally flat. It has four slots on each side of the panel to accommodate panel 141 to flex toward the spine when the cords are engaged so as to fit into the lordatic curve of the lumbar spine. In addition to this vertical flexing of central vertical column 147, which runs down the entire central vertical length of panel 141, ribs 153 and 157 may independently flex transversely and/or horizontally, either at the same time or at different times than the vertical flexion of column 147. Each rib 153 and 157 therefore has a slight lip 152 (0.0020") along its edge so as not to fatigue and split with repetitive flexions, and raised support center 149 provides added stability and strength.

A second aspect of the present invention is directed to an orthotic method that includes any of the components and techniques substantially as described above. Other embodiments, techniques or devices can also or alternately be used in this method aspect of the invention.

While it is apparent that the illustrative embodiments of the invention disclosed herein fulfill the objectives of the present invention, it is appreciated that numerous modifications and other embodiments may be devised by those skilled in the art. Additionally, feature(s) and/or element(s) from any embodiment may be used singly or in combination with other embodiment(s). Therefore, it will be understood that the appended claims are intended to cover all such modifications and embodiments that would come within the spirit and scope of the present invention.

We claim:

1. A back orthosis, comprising:

first and second, separate, opposing and mating front attachment panels, which are operatively and releasably attached to one another to form a circumferential enclosure about a wearer, the releasably attached first and second, separate, opposing and mating front attachment panels together forming at least one anterior anchoring point configured to fit centrally over a wearer's anterior side, opposite ends of the first and second, separate, opposing and mating front attachment panels each including at least one rear lateral anchoring point configured to fit over lateral positions of a wearer's back; and a separate, laterally adjustable, rigid lumbar compression piece configured for positioning only at the back of a wearer and having:

opposing first and second lateral sides, the first side connected along substantially its entire vertical length to the first, separate, opposing and mating front attachment panel by a first cord, and the second side connected along substantially its entire vertical length to the second, separate, opposing and mating front attachment panel by a second cord;

a first set of apertures through which the first cord passes and is operatively pulled or allowed to loosen, respectively either:

to draw the first side laterally closer to the first, separate, opposing and mating front attachment panel, and the first separate, opposing and mating front attachment panel posteriorly closer to the first side, or to distance the first side laterally further from the first, separate, opposing and mating front attachment panel, and the first, separate, opposing and mating front-attachment panel further from the first side; and a second set of apertures through which the second cord passes and is operatively pulled or allowed to loosen, respectively either:

to draw the second side laterally closer to the second, separate, opposing and mating front attachment panel, and the second separate, opposing and mating front attachment panel posteriorly closer to the second side, or to distance the second side laterally further from the second, separate, opposing and mating front attachment panel, and the second, separate, opposing and mating front attachment panel further from the second side;

wherein pulling of the first cord and the second cord causes the back orthosis to circumferentially tighten and to concentrate inward compression of the separate, laterally adjustable, rigid lumbar compression piece especially upon a spinal region of a wearer's back with the aid of a mechanical advantage dependent upon a number of apertures through which the first cord or the second cord passes.

2. The back orthosis of claim 1, wherein pulling of the first cord or the second cord causes relatively greater inward compression directly and especially upon a spinal region of a wearer's back than upon a region laterally adjacent to the spinal region of a wearer's back.

3. The back orthosis of claim 1, wherein at least one of the first set of apertures and the second set of apertures is formed by raised eyelets that are substantially parallel to a wearer's back when the separate, laterally adjustable, rigid lumbar compression piece is worn.

4. The back orthosis of claim 1, wherein the first and second, separate, opposing and mating front attachment panels have anterior portions that have greater rigidity than lateral sides of the first and second, separate, opposing and mating front attachment panels, which provides a vice-like frontal force diametrically opposed to the concentrated inward compression of the separate, laterally adjustable, rigid lumbar compression piece directly and especially upon a spinal region of a wearer's back.

5. The back orthosis of claim 1, wherein the separate, laterally adjustable, rigid lumbar compression piece has a raised, laterally beveled inner surface that operatively abuts against a spinal region of a wearer's back.

6. The back orthosis of claim 1, wherein the separate, laterally adjustable, rigid lumbar compression piece has a flat, curved, regular, irregular, or form-fitting inner compression surface and a generally flat, curved, regular, irregular, or form-fitting outer surface.

7. The back orthosis of claim 1, wherein the separate, laterally adjustable, rigid lumbar compression piece has at least four slots on each of the opposing first and second lateral sides through which the respective first cord and second cord pass.

8. The back orthosis of claim 1, further comprising:
at least one tensioning handle with respect to which the first cord passes and with respect to which a portion of the first cord changes its relative position in accordance with variations in upper and lower first cord lengths, relative to one another, each of which running between the at least one tensioning handle and the first set of apertures.

9. The back orthosis of claim 8, wherein every portion of the first cord changes its position with respect to the tensioning handle at least in accordance with adjustable vertical and circumferential stationary tensioning handle attachment positions on the first or second, separate, opposing and mating front attachment panels.

10. The back orthosis of claim 1, further comprising:
a pad configured to be positioned between a wearer's back and the rigid lumbar compression piece, wherein foam within the pad flows.

11. The back orthosis of claim 1, wherein the rigid lumbar compression piece comprises a horizontally and vertically centered, reinforced grid that is bordered by an upper and lower hollowed out, beveled bowls, the bottoms of which push against a spinal region of a wearer's back.

12. The back orthosis of claim 1, wherein a first lateral side of the opposing first and second lateral sides of the separate, laterally adjustable, rigid lumbar compression piece is immediately adjacent to at least one vertically centered aperture, through which the first cord passes before it passes through a final aperture on the separate, laterally adjustable, rigid lumbar compression piece just before extending to a manually operated tensioning handle.

13. The back orthosis of claim 12, wherein the at least one vertically centered aperture is a pair of side-by-side apertures, through each of which one of two opposing lengths of the first cord passes.

14. The back orthosis of claim 1, wherein the separate, laterally adjustable, rigid lumbar compression piece includes:
a central vertical axis about which a plurality of transversely and horizontally flexible extensions project to form each of the opposing first and second lateral sides.

15. The back brace of claim 14, wherein the plurality of transversely and horizontally flexible extensions each correspond to at least one aperture of the first set of apertures or at least one aperture of the second set of apertures.

16. The back brace of claim 1, wherein the separate, laterally adjustable, rigid lumbar piece further includes:
a plurality of independent horizontally disposed extensions at each of the opposing first and second lateral sides, each extension being configured to operatively flex in accordance with varying contours of lumbar and thoracic regions of a spinal region of a wearer's back that vary from individual-to-individual, with a finger-like horizontal and transverse motion when engaged in tension by the first cord or the second cord.

17. An orthotic method comprising utilizing a back orthosis according to claim 1.

* * * * *